US008461338B2

(12) United States Patent
Arad et al.

(10) Patent No.: US 8,461,338 B2
(45) Date of Patent: *Jun. 11, 2013

(54) (1R, 1'R)-ATRACURIUM SALTS SEPARATION PROCESS

(75) Inventors: Oded Arad, Rehovot (IL); Elena Ostrovsky, Rishon Le-Zion (IL)

(73) Assignee: Chemagis Ltd., Bnei Brak (IL)

(*) Notice: Subject to any disclaimer, the term of this patent is extended or adjusted under 35 U.S.C. 154(b) by 560 days.

This patent is subject to a terminal disclaimer.

(21) Appl. No.: 12/529,269

(22) PCT Filed: Mar. 5, 2008

(86) PCT No.: PCT/IL2008/000289
§ 371 (c)(1),
(2), (4) Date: Dec. 16, 2009

(87) PCT Pub. No.: WO2008/107887
PCT Pub. Date: Sep. 12, 2008

(65) Prior Publication Data
US 2010/0099878 A1    Apr. 22, 2010

Related U.S. Application Data

(60) Provisional application No. 60/893,749, filed on Mar. 8, 2007.

(51) Int. Cl.
*C07D 401/12* (2006.01)
(52) U.S. Cl.
USPC ............................................ 546/140
(58) Field of Classification Search
USPC ............................................ 546/140
See application file for complete search history.

(56) References Cited

U.S. PATENT DOCUMENTS

| | | | |
|---|---|---|---|
| 4,179,507 A | 12/1979 | Stenlake et al. | |
| 4,491,665 A | 1/1985 | El-Sayad et al. | |
| 4,701,460 A | 10/1987 | El-Sayad et al. | |
| 4,761,418 A | 8/1988 | Swaringen, Jr. et al. | |
| 4,851,537 A | 7/1989 | Noyori et al. | |
| 4,988,815 A | 1/1991 | Andre et al. | |
| 5,240,939 A | 8/1993 | Demko | |
| 5,453,510 A | 9/1995 | Hill et al. | |
| 5,556,978 A * | 9/1996 | Hill et al. ........................ 546/140 |
| 5,684,154 A | 11/1997 | Chamberlin et al. | |
| 6,015,903 A | 1/2000 | Viergutz et al. | |
| 6,177,445 B1 | 1/2001 | Bigham et al. | |
| 6,187,789 B1 | 2/2001 | Bigham et al. | |
| 6,830,933 B2 | 12/2004 | Lemmens et al. | |
| 7,265,099 B1 | 9/2007 | Bom et al. | |
| 2006/0009485 A1 | 1/2006 | Friedman et al. | |
| 2008/0139482 A1 | 6/2008 | Savarese | |
| 2009/0156562 A1 | 6/2009 | Winch | |
| 2010/0016596 A1 | 1/2010 | Pozzoli et al. | |
| 2010/0087650 A1 | 4/2010 | Ostrovsky et al. | |
| 2010/0168431 A1 | 7/2010 | Naddaka et al. | |
| 2010/0174082 A1* | 7/2010 | Arad et al. ........................ 546/140 |
| 2010/0184988 A1 | 7/2010 | Naddaka et al. | |
| 2010/0234602 A1 | 9/2010 | Arad et al. | |
| 2010/0256381 A1 | 10/2010 | Arad et al. | |
| 2010/0298570 A1 | 11/2010 | Segnalini et al. | |
| 2011/0185796 A1 | 8/2011 | Arad et al. | |

FOREIGN PATENT DOCUMENTS

| | | |
|---|---|---|
| CN | 101084896 A | 12/2007 |
| CN | 101337935 A | 1/2009 |
| CN | 101337936 A | 1/2009 |
| CN | 101475530 A | 7/2009 |
| CN | 101845017 A | 9/2010 |
| EP | 0 219 616 | 4/1987 |
| EP | 0219616 | 4/1987 |
| WO | WO 92/00965 A1 | 1/1992 |
| WO | WO 98/42675 A1 | 10/1998 |
| WO | WO 2007/091753 A1 | 8/2007 |
| WO | WO 2008/117271 A1 | 10/2008 |
| WO | WO 2008/132746 A1 | 11/2008 |
| WO | WO 2008/132748 A1 | 11/2008 |
| WO | WO 2008/155752 A1 | 12/2008 |
| WO | WO 2009/007946 A1 | 1/2009 |
| WO | WO 2009/057086 A1 | 5/2009 |
| WO | WO 2009/106547 A1 | 9/2009 |
| WO | WO 2009/133556 A2 | 11/2009 |
| WO | WO 2010/128518 A2 | 11/2010 |
| WO | WO 2010/128519 A1 | 11/2010 |

OTHER PUBLICATIONS

Ariffin et al., Journal of Chromatograph, B (2006), 842(2), p. 91-97.*
Lindon et al. "Directly coupled HPLC-NMR and HPLC-NMR-MS in pharmaceutical research and development," Journal of Chromatography B : Biomedical Applications, Elsevier Science Publishers, NL, vol. 748, No. 1, pp. 233-258 (Oct. 1, 2000).
Liu et al. "High-performance liquid chromatography of atracurium besylate," Yao Hsueh Hsueh Pao—Acta Pharmaceutica Sinica, Beijing, CN, vol. 29, No. 1, pp. 68-73 (Jan. 1, 1994).
Mistry et al. "Directly Coupled Chiral HPLC-NMR and HPLC-CD Spectroscopy as Complementary Methods for Structural and Enantiomeric Isomer Identification: Application to Atracurium Besylate," Analytical Chemistry, vol. 71, No. 14, pp. 2838-2843 (1999).
Nehmer "Separation of cis-cis, cis-trans and trans-trans isomers of (.+-.)-atracurium besylate and cis and trans isomers of its major quaternary decomposition products and related impurity by reversed-phase high-performance liquid chromatography," Journal of Chromatography, vol. 457, pp. 127-135 (1988).
Stenlake et al.: "Biodegradable Neuromuscular Blocking Agents 6. Stereochemical Studies on Atracurium and Related Polyalkylene Diesters," European Journal of Medicinal Chemistry, Editions Scientifique Elsevier, Paris, FR, vol. 19, No. 5, pp. 441-450 (Jan. 1, 1984).
Stenlake et al., "Neuromuscular Block Agents: Some approaches to short acting compounds," European Journal of Medicinal Chemistry, vol. 27, No. 5, pp. 463-477 (1992).

(Continued)

Primary Examiner — Yong Chu
(74) Attorney, Agent, or Firm — Leydig, Voit & Mayer, Ltd.

(57) ABSTRACT

The present invention provides an improved method of chromatographically separating the isomers of (1R,rR)-atracurium salts by high-performance liquid chromatography (HPLC), in the absence of a strong acid. The separation is preferably performed on a silica gel HPLC column using an eluent containing an organic solvent, a polar aprotic co-solvent and a weak organic acid.

21 Claims, 3 Drawing Sheets

OTHER PUBLICATIONS

ICH Guideline, International Conference on Harmonization of Technical Requirements of Registration of Pharmaceuticals for Human Use (ICH), ICH Q3CR4 residual solvents MEDIA5254 (Feb. 2009).

European Patent Office, International Search Report in International Patent Application No. PCT/IL2008/000291 (Jul. 4, 2008).

European Patent Office, International Search Report in International Patent Application No. PCT/IL2008/000290 (Jul. 7, 2008).

European Patent Office, International Search Report in International Patent Application No. PCT/IL2008/000289 (Sep. 5, 2008).

European Patent Office, International Search Report in International Patent Application No. PCT/IL2008/000586 (Aug. 27, 2008).

European Patent Office, International Search Report in International Patent Application No. PCT/IL2008/000589 (Aug. 21, 2008).

European Patent Office, International Search Report in International Patent Application No. PCT/IL2008/000590 (Aug. 29, 2008).

European Patent Office, International Search Report in International Patent Application No. PCT/IL2008/001329 (Feb. 4, 2009).

U.S. Patent & Trademark Office, International Search Report in International Patent Application No. PCT/IL2009/000452 (Aug. 12, 2009).

* cited by examiner

(1R, 1'R)-ATRACURIUM SALTS SEPARATION PROCESS

TECHNICAL FIELD

The present invention relates to chromatography and more particularly to an improved method of separating the (1R, 1'R)-atracurium salt isomers by means of high pressure liquid chromatography (HPLC).

BACKGROUND OF THE INVENTION

Cisatracurium besylate has the chemical name (1R,1'R,2R, 2'R)-2,2'-[1,5-pentanediylbis[oxy(3-oxo-3,1-propanediyl)]] bis[1-[(3,4-dimethoxyphenyl)methyl]-1,2,3,4-tetrahydro-6, 7-dimethoxy-2-methyl-isoquinolinium dibenzenesulfonate and is represented by the structural formula (I) below:

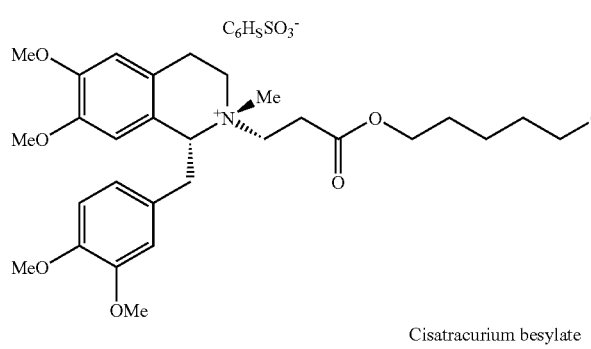

Cisatracurium besylate

Cisatracurium besylate is the dibenzenesulfonate salt of 1R-cis,1'R-cis isomer of atracurium (i.e., two molecules of benzenesulfonate per one diammonium molecule of cisatracurium). Cisatracurium besylate is one of the 10 possible isomers of atracurium besylate and constitutes approximately 15% of that mixture (atracurium has four chiral centers, two on each half of the molecule, one at each of the nitrogen atoms and the other at position 1 in each of the tetrahydroisoquinolinium rings so theoretically there are expected 16 possible isomers; however, due to the symmetry of the molecule, the number of atracurium isomers is reduced to 10).

Cisatracurium besylate is a nondepolarizing neuromuscular blocking agent indicated for inpatients and outpatients as an adjunct to general anesthesia, to facilitate tracheal intubation, and to provide skeletal muscle relaxation during surgery or mechanical ventilation in the Intensive Care Unit (ICU).

Cisatracurium besylate possesses an activity that is superior to atracurium besylate, with significantly less side effects.

Cisatracurium besylate is marketed in the United States and Europe by Glaxo Wellcome and Abbott Laboratories under the trade name Nimbex®, which is a sterile, non-pyrogenic aqueous solution that is adjusted to pH 3.25 to 3.65 with benzenesulfonic acid. The drug is provided in 2.5 ml, 5 ml and 10 ml ampules having a strength of 2 mg/ml cisatracurium besylate. In addition, a 30 ml vial containing 5 mg/ml cisatracurium besylate is also available.

Cisatracurium besylate slowly loses potency with time at a rate of approximately 5% per year under refrigeration (5° C.). Nimbex should be refrigerated at 2° to 8° C. (36° to 46° F.) in the carton to preserve potency. The rate of loss in potency increases to approximately 5% per month at 25° C. (77° F.).

Atracurium besylate is disclosed in U.S. Pat. No. 4,179, 507 (hereinafter U.S. '507), which describes a series of bis veratryl isoquinolinium quaternary ammonium salts, including atracurium besylate. The synthesis of atracurium besylate, as taught in U.S. '507, involves the coupling of (±)-tetrahydropapaverine base, compound (II), with 1,5-pentamethylene diacrylate, compound Treatment of the resulting tertiary amine base with oxalic acid results in the isolation of N,N'-4,10-dioxa-3,11-dioxotridecylene-1,13-bis-tetrahydropapaverine dioxalate, compound (IV). The dioxalate salt (compound (IV) is converted to the free base, compound (V), with sodium bicarbonate solution and extracted into toluene. After evaporation of the toluene, the residue is dissolved in acetonitrile and treated with methyl benzenesulfonate. The addition of diethyl ether results in the precipitation of atracurium besylate, compound (VI), which is subsequently filtered and dried. Scheme 1 below illustrates the chemical pathway described above.

Scheme 1

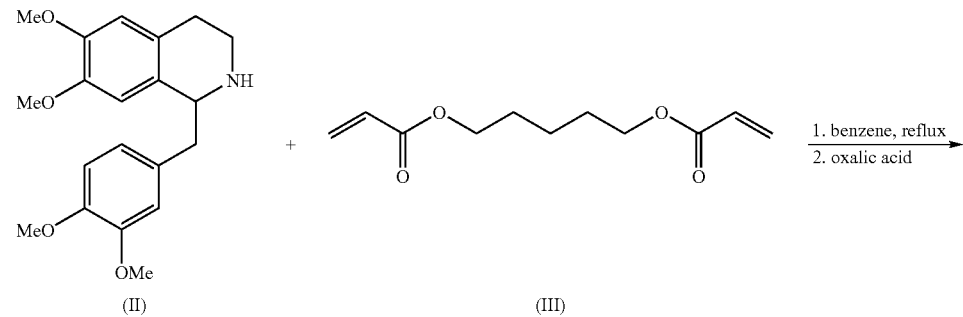

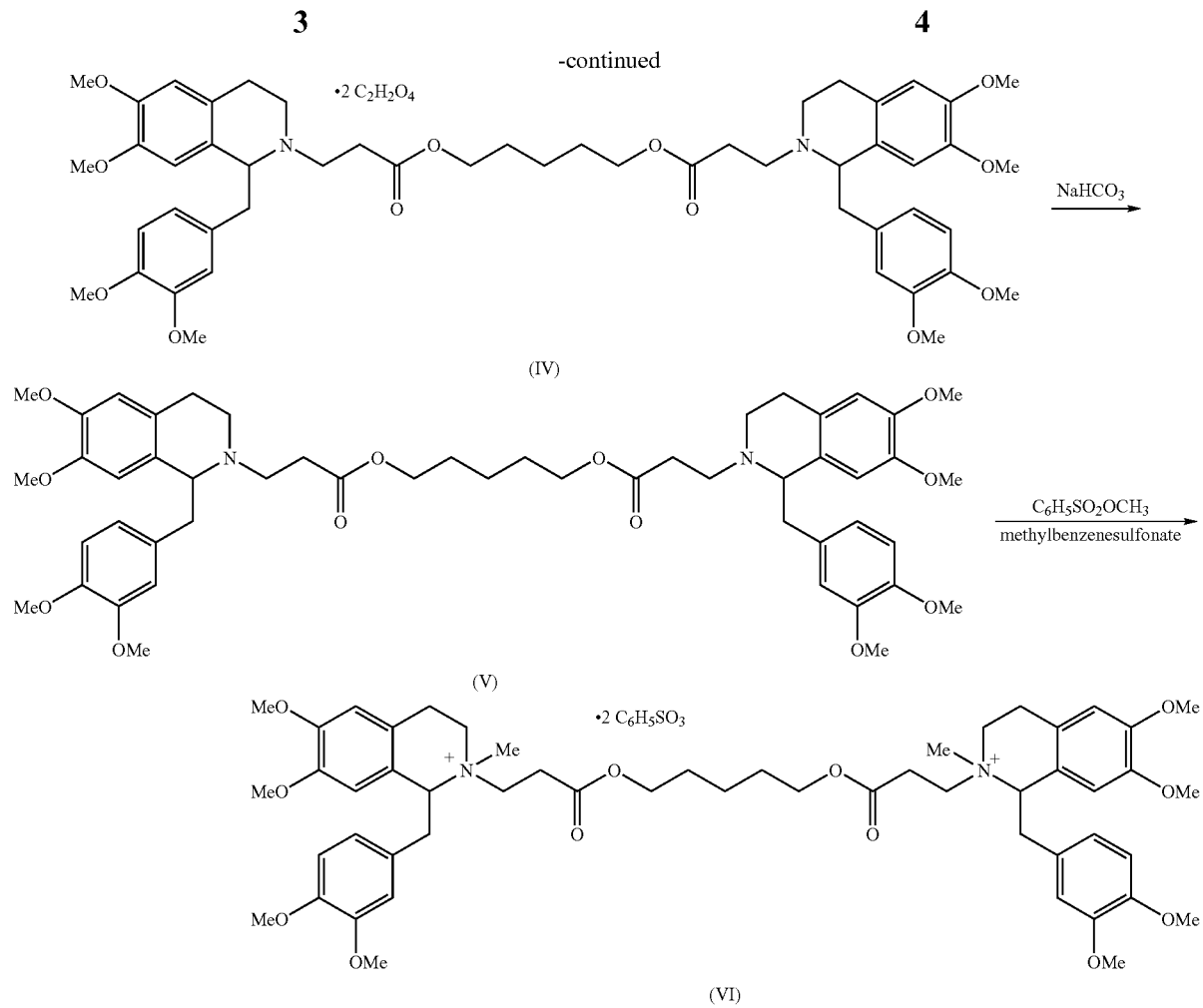

U.S. '507 teaches that the stereoisomerism of atracurium besylate (VI) may be partly controlled by the use of compound (II) of a defined stereochemical configuration and thus provide the tertiary amine base (V) of a RR-, SS-, or RS-(meso) configuration. The quaternisation process introduces another two centers of asymmetry with the resulting formation of a mixture of stereoisomers. However, the '507 patent makes no attempt at separating the mixture of stereoisomers.

Cisatracurium besylate is disclosed in U.S. Pat. Nos. 5,453,510 (hereinafter U.S. '510), and 5,556,978 (hereinafter U.S. '978), which describe forming (R)-tetrahydropapaverine from compound (II), and the conversion of compound (II) into a mixture of R and S diastereoisomer salts with the chiral amino acid, N-acetyl-L-leucinate, comprising 83% of the R and 17% of the S diastereoisomer. Crystallization of the mixture from acetone affords 97% (R)-tetrahydropapaverine-N-acetyl-L-leucinate and 3% (S)-tetrahydropapaverine-N-acetyl-L-leucinate, which is treated with aqueous ammonia and toluene to afford (R)-tetrahydropapaverine base, which is isolated from the toluene layer. The (R)-tetrahydropapaverine is subsequently reacted with 1,5-pentamethylene diacrylate followed by oxalic acid to afford the dioxalate salt of the bis tertiary amine base, (1R,1'R)-2,2'-(3,11-dioxo-4,10-dioxamidecamethylene)-bis-(1,2,3,4-tetrahydro-6,7-dimethoxyveratryl-isoquinoline, Conversion of the dioxalate salt to the bis tertiary amine base with sodium carbonate followed by treatment with methyl benzenesulfonate affords an aqueous solution of (1R,1'R)-atracurium besylate which is subjected to lyophilisation. The resulting pale yellow solid consists of a mixture of three isomers, namely, 1R-cis,1'R-cis; 1R-cis,1'R-trans; 1R-trans,1'R-trans (hereinafter referred to as the (1R,1'R)-atracurium besylate isomer mixture) in a ratio of about 58:34:6 respectively. The (1R,1'R)-atracurium besylate isomer mixture is subjected to preparative HPLC column chromatography on silica using a mixture of dichloromethane, methanol and benzenesulfonic acid in the ratio of 4000:500:0.25 as the eluent. The fractions containing the required isomer are collected and washed with water. The dichloromethane solution is evaporated to dryness, the residue dissolved in water and the pH of the solution adjusted to 3.5-4.0 with an aqueous solution of benzenesulfonic acid. The aqueous solution is lyophilized to afford cisatracurium besylate possessing an isomeric purity of about 99%. Both U.S. '510 and U.S. '978 describe performing the high-performance liquid chromatography separation in the presence of a strong acid which include benzenesulfonic acid, methanesulfonic acid, p-toluenesulfonic acid or phosphoric acid. In addition, an alcohol such as methanol, ethanol or n-propanol is required for the isomer separation.

However, HPLC methods for separating the isomers of (1R,1'R)-atracurium besylate that apply strong acids may be unsatisfactory for large scale production because stainless steel (commonly used in HPLC instruments) is not compatible with strong acids (such as benzenesulfonic acid) due to an excessive corrosion of stainless steel components resulting in the possible contamination of the product, which is also undesirable, especially on large scale. Therefore, there is a need for improved methods, that avoid using strong acids, for separating the (1R,1'R)-atracurium besylate isomer mixture, particularly on a large scale. The present invention provides such methods.

BRIEF SUMMARY OF THE INVENTION

The present invention provides an improved chromatographic method of separating the isomers of (1R,1'R)-atracurium salts (e.g. the besylate salt), i.e., (1R-cis,1'R-cis), (1R-cis,1'R-trans), and (1R-trans,1R-trans) isomers, which avoids the use of strong acids. Good separation as well as improved stability of the 1R-cis,1'R-cis cisatracurium besylate isomer can be achieved in accordance with the present invention. The method of chromatographically separating the (1R,1'R)-atracurium salts (e.g. the besylate salt) isomer mixture uses mixtures of an organic solvent, a polar aprotic co-solvent and a weak acid as eluent. In a preferred embodiment of the present invention, the weak acid is an organic acid. The improved chromatographic method of separating the (1R,1'R)-atracurium salts (e.g., the besylate salt) isomer mixture provides also the elimination of other substances.

The method of separating the isomers of (1R,1'R)-atracurium salts (e.g., the besylate salt) preferably includes the steps of:

(a) dissolving an isomer mixture of (1R,1'R)-atracurium salt (e.g., the besylate salt) in at least one organic solvent;

(b) applying the isomer mixture solution to an HPLC column containing a suitable stationary phase;

(c) eluting the column with a mobile phase containing an organic solvent, a polar aprotic co-solvent and a weak acid;

(d) collecting the fractions containing the 1R-cis,1'R-cis isomer;

(e) optionally performing an ion exchange step to introduce the besylate anion; and (f) isolating the 1R-cis,1'R-cis isomer (e.g., cisatracurium besylate).

The present invention additionally provides a method for isolating 1R-cis,1'R-cis isomer of atracurium besylate obtained in accordance with the separation process of the present invention. The method for isolating the 1R-cis,1'R-cis isomer of atracurium besylate preferably includes the steps of:

(a) combining eluted fractions, which preferably contain at least 90% of the 1R-cis,1'R-cis isomer;

(b) washing the combined eluted fractions with acidic brine and separating the phases;

(c) drying the organic phase and evaporating the solvent to obtain a residual oil;

(d) dissolving the oil in a solvent; and (e) optionally isolating the product, e.g., by lyophilizing the solution or by precipitation.

The method for isolating the 1R-cis,1'R-cis isomer of cisatracurium besylate further optionally includes performing an ion exchange, e.g., via a strong anion exchange column or cartridge (hereinafter SAX).

A particularly preferred embodiment includes performing high-performance liquid chromatography (HPLC) separation using a column packed with silica, eluting with a mobile phase, which includes a mixture of an organic solvent in combination with a polar aprotic co-solvent and a weak acid, e.g., dichloromethane, DMSO and formic acid. Preferably, the dichloromethane:DMSO:formic acid ratio in the eluent mixture is about 70-85 (dichloromethane):8-20 (DMSO):5-15 (formic acid). Exemplary eluent mixtures contain dichloromethane, DMSO and formic acid in ratios of e.g., 75:15:10, 78:13:9 and 80:10:10.

In accordance with the present invention, the desired 1R-cis,1'R-cis isomer can be obtained in high isomeric purity, e.g., greater than 99.5%.

DETAILED DESCRIPTION OF THE INVENTION

Figure 1:
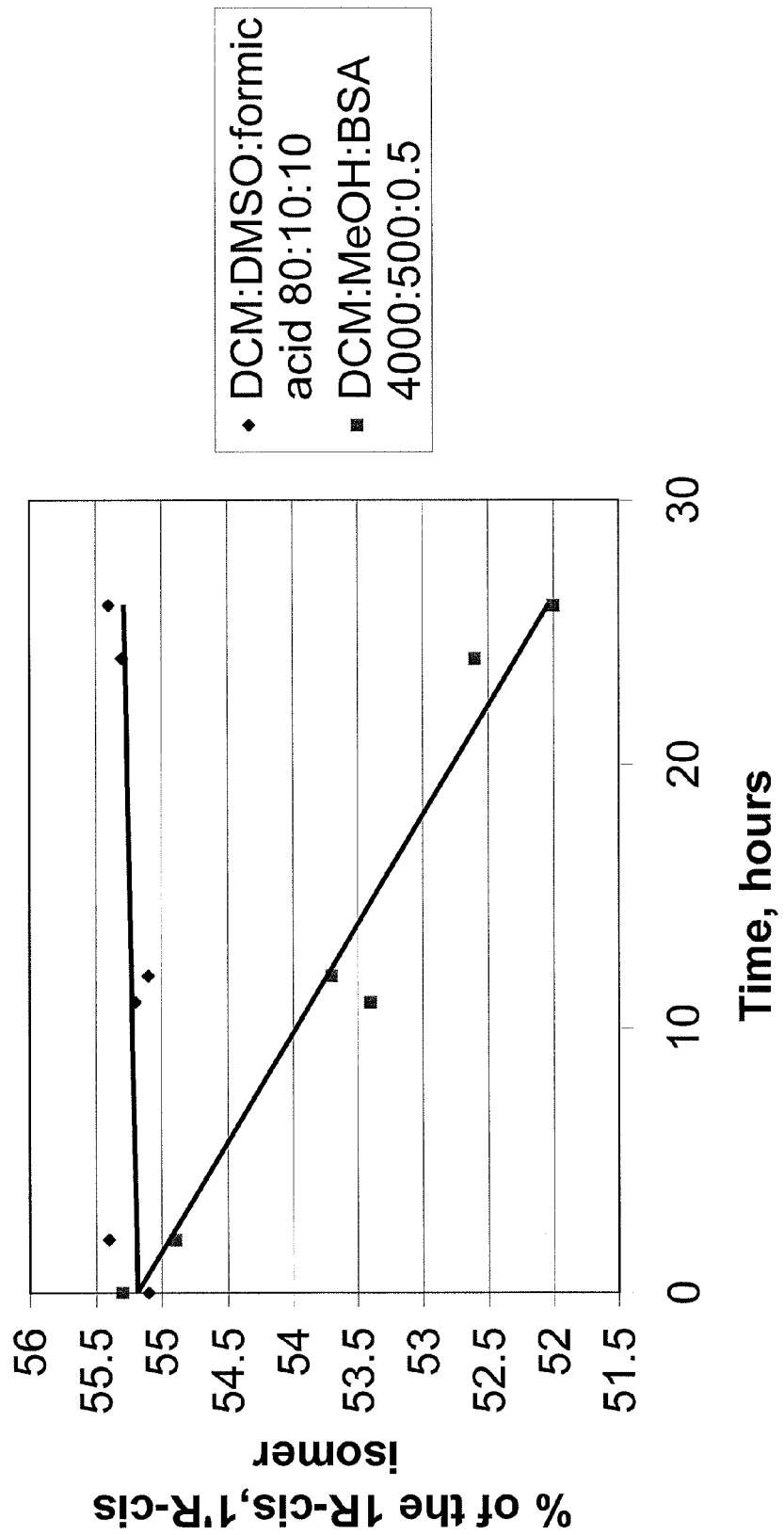
FIG. 1 depicts the stability of the 1R-cis,1'R-cis isomer in the eluent mixture at 25° C. as a function of time.

The present invention provides an improved chromatographic method of separating the (1R,1'R)-atracurium salts (e.g., the besylate salt) isomer mixture, which avoids the use of strong acids in the eluent mixture. The method of the present invention allows for the separation of the 1R-cis,1'R-cis isomer from an isomer mixture of (1R,1'R)-atracurium salt (e.g., the besylate salt) and other compounds present.

The inventors of the present invention have found that the 1R-cis,1'R-cis isomer, obtained by HPLC separation as described in U.S. '510 and U.S. '978, is unstable in the eluent mixture and leads to the formation of decomposition products. Surprisingly, it has been further found by the inventors of the present invention, that good separation as well as improved stability of the 1R-cis,1'R-cis isomer can be achieved when the eluent contains a polar aprotic co-solvent and a weak acid, which is preferably an organic acid, thus the use of strong acid can be avoided.

The term "strong acids" refers to acids that dissociate practically completely (>99%) in aqueous solutions at standard temperature and pressure, such as benzenesulfonic acid, having a pKa of 0 and lower, while the term "weak acids" refers to acids that do not dissociate completely in aqueous solutions, such as acetic acid, having a pKa value of 2.5 or higher.

The term "(1R,1'R) atracurium besylate isomer mixture" refers to a mixture of the (1R-cis,1'R-cis), (1R-cis,1'R-trans) and (1R-trans,1'R-trans) isomers, while the term "cisatracurium besylate" refers to the 1R-cis,1'R-cis isomer.

The term "isomeric purity" as used herein, refers to the area percent of the peak corresponding to the 1R-cis,1'R-cis isomer relative to the total area percent of the (1R-cis,1'R-cis), (1R-cis,1'R-trans) and (1R-trans,1'R-trans) isomers.

In one embodiment, the present invention provides a method of separating isomers of (1R,1'R)-atracurium salt (e.g., the besylate salt), which includes the steps of:

(a) dissolving the (1R,1'R)-atracurium salt (e.g., the besylate salt) isomer mixture in at least one organic solvent;

(b) applying the (1R,1'R)-atracurium salt (e.g., the besylate salt) isomer mixture to an HPLC column containing a suitable stationary phase;

(c) eluting the column with a mobile phase containing an organic solvent, a polar aprotic co-solvent and a weak acid;

(d) collecting the fractions containing the 1R-cis,1'R-cis isomer;

(e) optionally performing an ion exchange step as needed to introduce the besylate anion; and (f) isolating the 1R-cis,1'R-cis isomer (e.g., cisatracurium besylate).

The isomer separation is effected by using a suitable stationary phase (a solid support), which is capable of separating the 1R-cis,1'R-cis isomer from an isomeric mixture of (1R,1'R)-atracurium salt (e.g., the besylate salt). Suitable solid supports can include, for example, silica gel.

The molar concentration (M) of the (1R,1'R)-atracurium salt (e.g., the besylate salt) isomer mixture in the solution that is applied to the HPLC column is in the range from about 0.1 M to about 0.5 M, preferably from about 0.1 M to about 0.3 M.

The organic solvent used in step (a) preferably includes dichloromethane, chloroform, 1,4-dioxane, or a mixture thereof. A preferred organic solvent includes dichloromethane.

The mobile phase, of step (c), preferably includes a mixture of an organic solvent, a polar aprotic co-solvent and a weak acid. Suitable polar aprotic co-solvents, which can be used in step (c), include dimethyl sulfoxide (DMSO), N,N-dimethylformamide (DMF), N,N-dimethylacetamide (DMA), N-methyl-2-pyrrolidone (NMP) or mixtures thereof. Preferably, the polar aprotic solvent includes DMSO.

The organic solvent used in step (c) preferably includes dichloromethane, chloroform, 1,4-dioxane, or a mixture thereof. A preferred organic solvent includes dichloromethane.

The weak acid of step (c) is preferably an organic acid, which includes formic acid, acetic acid, propionic acid or a mixture thereof. A particularly preferred weak organic acid includes formic acid.

The inventors of the present invention have found that good separation can be obtained using mixtures of e.g., dichloromethane/DMSO/formic acid. According to a preferred embodiment of the present invention the column is eluted with a mixture comprising dichloromethane, formic acid and DMSO. The dichloromethane:DMSO:formic acid ratio in the eluent mixture is about 70-85 (dichloromethane), 8-20 (DMSO) and 5-15 (formic acid). Exemplary eluent mixtures containing dichloromethane, DMSO and formic acid are in ratios of e.g., 75:15:10, 78:13:9 and 80:10:10 respectively.

In accordance with the present invention, an ion exchange step can be performed to afford the desired besylate anion.

In accordance with the present invention, the content of the 1R-cis,1'R-cis isomer remains unchanged after 26 hours in an eluent mixture comprising dichloromethane, DMSO and formic acid. By contrast, the content of the 1R-cis,1'R-cis isomer decreases in the eluent mixture employed in U.S. '978 (dichloromethane, methanol, and benzenesulfonic acid) by more than 3% after 26 hours at room temperature (see Example 5 and FIG. 1).

In another embodiment, the present invention provides a method of performing work-up procedure for isolating the 1R-cis,1'R-cis isomer, which includes the steps of:

(a) combining eluted fractions, which preferably contain at least 90% of the 1R-cis,1'R-cis isomer;

(b) washing the combined eluted fractions with acidic brine and separating the phases;

(c) drying the organic phase and evaporating the solvent to obtain a residual oil;

(d) dissolving the oil in a solvent; and (e) optionally isolating the product, e.g., by lyophilizing the solution or by precipitation.

Preferably, the solution used for washing the combined eluted fraction is 10% brine solution, which is acidified to pH 2 with a suitable acid, e.g., benzenesulfonic acid (BSA) or an aqueous solution of BSA. The term 10% brine, as defined herein, refers to 10% salt (NaCl) saturated aqueous solution.

According to the present invention, acidifying the combined eluted fraction is performed by using an aqueous BSA solution.

Precipitation is preferably carried out at least once from a solvent or a solvent mixture selected from tetrahydrofuran (THF), 2-methyl-tetrahydrofuran (2-Me-THF), diethyl ether, diisopropyl ether, methyl tert-butyl ether (MTBE), acetone, hexane, heptane, cyclohexane, and mixtures thereof.

Optionally, the solvent or solvent mixture can contain formic acid or brine acidified to pH 2 with, e.g., about a 0.6 mM aqueous BSA solution (hereinafter the aqueous acidic solution).

In another embodiment, the method of isolating the 1R-cis,1R-cis isomer of cisatracurium besylate further optionally includes performing ion exchange, e.g., via a strong anion exchange column or cartridge (SAX).

The present invention provides cisatracurium besylate, having an isomeric purity of greater than about 97%, preferably greater than about 99%, and more preferably greater than about 99.5%, as measured by HPLC, and preferably containing less than about 0.5% of other isomers.

Reference is now made to the following examples, which serve to illustrate the invention but without in any way limiting its scope.

EXAMPLE 1

This example demonstrates the chromatographic separation of (1R,1'R)-atracurium besylate isomer mixture.

The sample solution for preparative separation was applied to the chromatography column packed with silica. The column was eluted with a mixture of dichloromethane, DMSO and formic acid in a ratio of 78:13:9 respectively. Fractions of the column eluate were collected, and those fractions containing the required 1R-cis,1'R-cis isomer were combined.

Two additional runs were performed using the same isomer mixture as that in the first run. Table 1 summarizes the results for the three runs.

TABLE 1

| Run | Loading volume (ml) | Loading concentration (M) | % of the cis-cis isomer in the (1R,1'R)-atracurium mixture | % isomer purity of the obtained cis-cis isomer |
|---|---|---|---|---|
| 1 | 2 | 0.164 | 58 | 99.7 |
| 2 | 3 | 0.164 | 58 | 99.4 |
| 3 | 3 | 0.164 | 58 | 99.7 |

EXAMPLE 2

This example demonstrates isomer separation by HPLC using different weak organic acids in the eluent mixture.

A mixture of (1R,1'R)-atracurium besylate isomer mixture containing 58% 1R-cis,1'R-cis; 36% 1R-cis,1'R-trans and 6% 1R-trans,1'R-trans was applied to a silica column (Zorbax, Sil-RX, 250 mm×4.6 mm×5μ). The column was eluted with the following mixtures presented in Table 2 below.

TABLE 2

| Run | Flow ml/min | Eluent Composition | | | Result | | |
|---|---|---|---|---|---|---|---|
| | | Dichloromethane % volume | DMSO % volume | Acid (% vol.) | 1R,1'R-isomer | RT min | Resolution |
| 1 | 1.5 | 75 | 20 | Acetic (5) | cis-cis | 4.9 | — |
| | | | | | cis-trans | 6.8 | 3.5 |
| | | | | | trans-trans | 8.7 | 0.9 |
| 2 | 1.2 | 70 | 20 | Acetic (10) | cis-cis | 5.3 | — |
| | | | | | cis-trans | 6.8 | 3.5 |
| | | | | | trans-trans | 10.2 | 4.2 |
| 3 | 1.2 | 80 | 10 | Formic (10) | cis-cis | 6.7 | — |
| | | | | | cis-trans | 7.8 | 2.4 |
| | | | | | trans-trans | 11.2 | >5.0 |
| 4 | 1.2 | 60 | 30 | Propionic (10) | tis-cis | 3.7 | — |
| | | | | | cis-trans | 4.2 | 1.8 |
| | | | | | trans-trans | 7.8 | >3.5 | min = minutes.
Resolution = $2(t_2 - t_1)/(w_2 + w_1)$, wherein $t_2$, $t_1$ are the retention times (RT) of the eluted peaks; $w_2$, $w_1$ are the peak widths.

Figure 2:
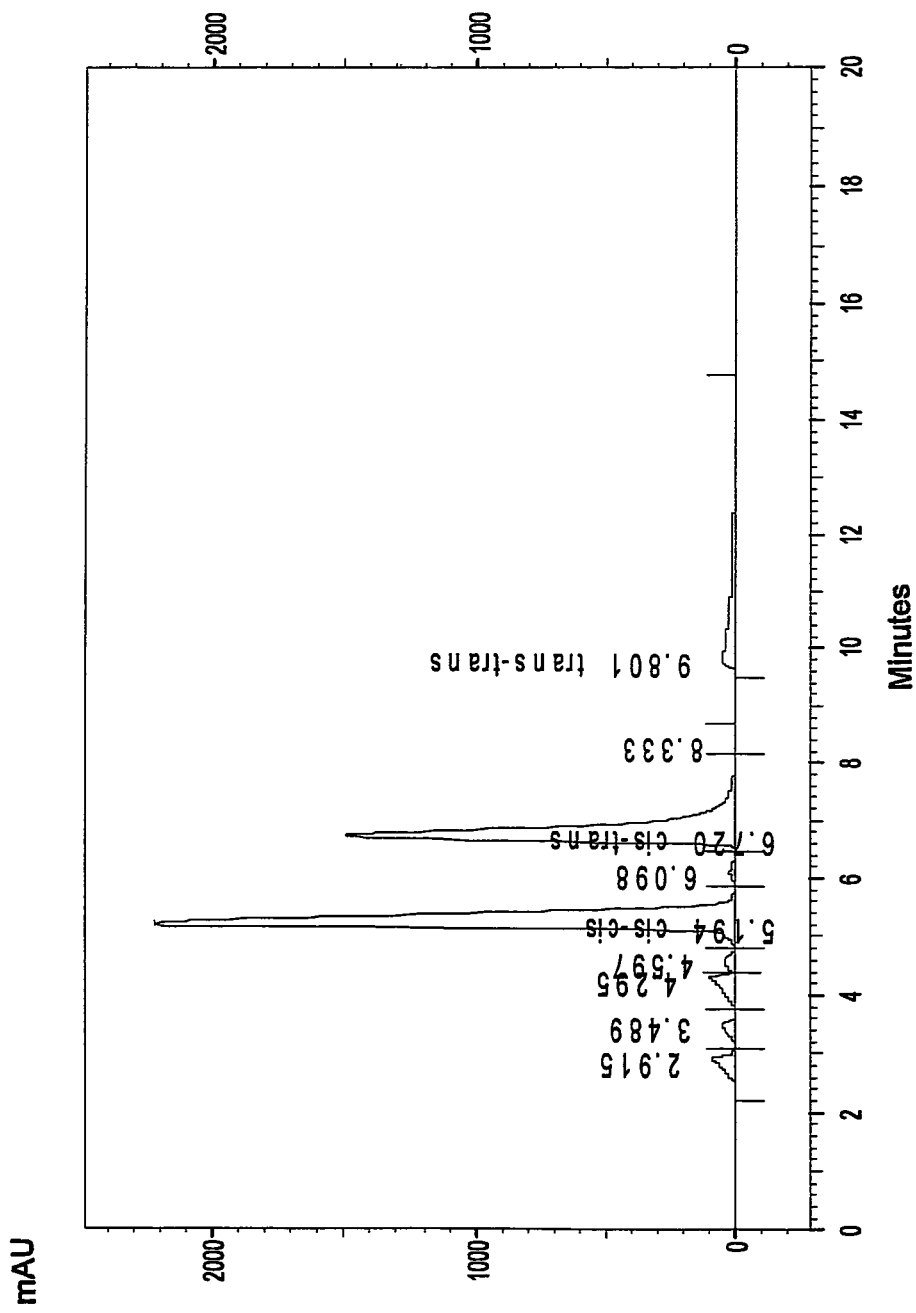
FIG. 2 depicts the chromatogram of (1R,1'R)-atracurium besylate isomer mixture prepared in accordance with the present invention.

A chromatogram of the product prepared according to Table 2, Run 2, is shown in FIG. 2. The following conditions were used:

Column: Zorbax, Sil-RX, 250 mm*4.6 mm*5μ, PN 880975-901
Mobile phase: DCM:DMSO:Acetic acid=70:20:10
Detection: 280 nm
Flow rate: 1.2 ml/min
Injection volume: 10 μl
Sample concentration: 15 mg/ml (Diluent-DCM On the basis of the above results given in the Table 2, acetic acid and propionic acid show good isomer separations similar to formic acid as demonstrated by the resolution results.

EXAMPLE 3

This example demonstrates isomer separation by HPLC using different polar aprotic solvents in the eluent mixture.

A mixture of (1R,1'R)-atracurium besylate isomers containing 58% 1R-cis,1'R-cis; 36% 1R-cis,1'R-trans and 6% 1R-trans,1'R-trans was applied to a silica column (Zorbax, Sil-RX, 250 mm×4.6 mm×5μ). N,N-dimethylformamide (DMF), N,N-dimethylacetamide (DMA) and N-methyl-2-pyrrolidone (NMP) were used in place of DMSO, as detailed in Table 3.

TABLE 3

| Run | Flow ml/min | Eluent Composition | | | Result | | |
|---|---|---|---|---|---|---|---|
| | | DCM % volume | Aprotic polar solvent (% volume) | Acid (% volume) | 1R,1'R-isomer | RT (min.) | Resolution |
| 1 | 1.0 | 75 | DMF (15) | Formic (10) | cis-cis | 22.3 | — |
| | | | | | cis-trans | 33.7 | >4.0 |
| | | | | | trans-trans | 53.7 | 5.3 |
| 2 | 1.5 | 75 | DMA (25) | Formic (10) | cis-cis | 10.3 | — |
| | | | | | cis-trans | 17.8 | >5.5 |
| | | | | | trans-trans | 32.3 | 6.3 |
| 3 | 0.8 | 55 | NMP (35) | Formic (10) | cis-cis | 7.6 | — |
| | | | | | cis-trans | 12.2 | 5.1 |
| | | | | | trans-trans | 16.3 | >7.0 |
| 4 | 1.5 | 58 | NMP (32) | Acetic (10) | cis-cis | 20.0 | — |
| | | | | | cis-trans | 40.2 | 3.6 |
| | | | | | trans-trans | ~80 | >7.0 |

DCM = dichloromethane

Figure 3:
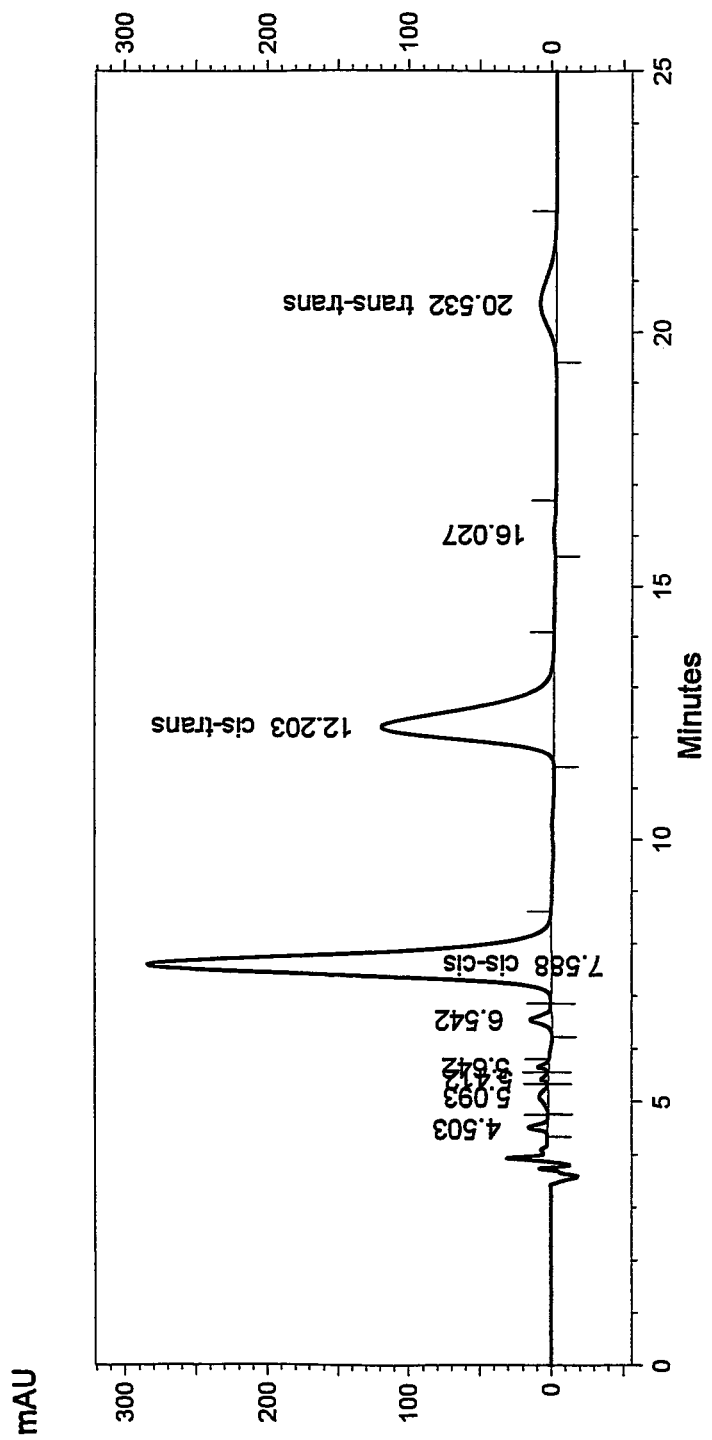
FIG. 3 depicts the chromatogram of (1R,1'R)-atracurium besylate isomer mixture using N-methyl-2-pyrrolidone as polar aprotic co-solvent in the eluent mixture.

A chromatogram of a (1R,1'R)-atracurium besylate isomer mixture separated using N-methyl-2-pyrrolidone as polar aprotic co-solvent in the eluent mixture is depicted in FIG. 3. The following conditions were used:

Column: ZORBAX RX-SIL, 5 u, 250*4.6 mm, PN880975-901
Eluent: dichloromethane:N-methyl-2-pyrrolidone:formic acid 55:35:10
Detector UV: 280 nm
Flow: 0.8 ml/min The following data apply to the chromatogram depicted in FIG. 3:

TABLE 4

| Pk # | Retention Time | Area | Area Percent | Theoretical plates (USP) | Resolution (USP) | Asymmetry | Height |
|---|---|---|---|---|---|---|---|
| 1 | 4.503 | 89811 | 0.64 | 10116 | 0.0 | 1.2 | 13177 |
| 2 | 5.093 | 100844 | 0.72 | 2257 | 1.9 | 0.0 | 6379 |
| 3 | 5.412 | 36558 | 0.26 | 14113 | 1.0 | 0.0 | 5098 |
| 4 | 5.642 | 45055 | 0.32 | 21886 | 1.4 | 0.0 | 7539 |
| 5 | 6.542 | 177872 | 1.27 | 7748 | 4.0 | 0.0 | 15024 |
| 6 | 7.588 | 7774644 | 55.56 | 1780 | 2.1 | 1.2 | 283833 |
| 7 | 12.203 | 4952618 | 35.39 | 2005 | 5.1 | 1.4 | 120704 |
| 8 | 16.027 | 35150 | 0.25 | 6144 | 4.0 | 0.0 | 1167 |
| 9 | 20.532 | 780050 | 5.57 | 1898 | 3.3 | 1.2 | 11177 |
| Totals | | 13992602 | 100.00 | | | | 464098 |

On the basis of the above results given in Table 3, DMF, DMA and NMP can be used in place of DMSO in the eluent mixture, as shown by the resolution results.

EXAMPLE 4

This example demonstrates isomer separation by HPLC using different organic solvents.

A mixture of (1R,1'R)-atracurium besylate isomer mixture containing 58% 1R-cis,1'R-cis; 36% 1R-cis,1'R-trans and 6% 1R-trans,1'R-trans was applied to a silica column (Zorbax, Sil-RX, 250 mm×4.6 mm×5µ). Chloroform and 1,4-dioxane were used in place of dichloromethane, as detailed in Table 5.

TABLE 5

| | | Eluent Composition | | | Result | | |
|---|---|---|---|---|---|---|---|
| Run | Flow ml/min | Organic solvent (% volume) | DMSO % volume | Weak acid (% volume) | 1R,1'R-isomer | RT (min.) | Resolution |
| 1 | 1.0 | Chloroform (80) | 10 | Formic (10) | cis-cis | 9.5 | — |
| | | | | | cis-trans | 11.5 | 2.8 |
| | | | | | trans-trans | 16.0 | >4.0 |
| 2 | 1.0 | Chloroform (70) | 20 | Acetic (10) | cis-cis | 7.4 | — |
| | | | | | cis-trans | 9.9 | >2.2 |
| | | | | | trans-trans | 13.8 | >5.6 |
| 3 Gradient | 1.0 | 1,4-dioxane (85) t = 0 min | 5 | Formic (10) | cis-cis | 15.0 | — |
| | | | | | cis-trans | 18.4 | 3.7 |
| | | 1,4-dioxane (75) t = 20 min | 15 | Formic (10) | trans-trans | 21.8 | 3.1 |

On the basis of the above results given in the table, both chloroform and 1,4-dioxane can be used in place of dichloromethane in the eluent mixture as shown by the resolution results.

EXAMPLE 5

This example demonstrates the stability of cisatracurium salt in different eluent mixtures.

Table 6 illustrates how the amount of the 1R-cis,1'R-cis isomer changes at room temperature as a function of time in 3 different eluent mixtures. The (1R,1'R)-atracurium besylate isomer mixture was dissolved in the eluent and the resulting solutions were allowed to stand at room temperature for a period of 26 hours. After certain time intervals, as specified in Table 6, samples were withdrawn from each one of the 3 solutions and assayed by HPLC to determine the amount of the 1R-cis,1'R-cis isomer in the mixture.

TABLE 6

| | | % of the 1R-cis,1'R-cis isomer in the eluent composition* | | |
|---|---|---|---|---|
| Conditions | Time (hours) | dichloromethane: DMSO: formic acid 80:10:10 (A) | dichloromethane: DMSO: benzenesulfonic acid 90:10:0.006 (B) | dichloromethane: methanol: benzenesulfonic acid 4000:500:0.5 (C) |
| Room temperature | 0 | 55.1 | 55.3 | 55.3 |
| | 2 | 55.4 | 55.3 | 54.9 |

TABLE 6-continued

| | | % of the 1R-cis,1'R-cis isomer in the eluent composition* | | |
|---|---|---|---|---|
| Conditions | Time (hours) | dichloromethane: DMSO: formic acid 80:10:10 (A) | dichloromethane: DMSO: benzenesulfonic acid 90:10:0.006 (B) | dichloromethane: methanol: benzenesulfonic acid 4000:500:0.5 (C) |
| | 11 | 55.2 | 55.3 | 53.4 |
| | 12 | 55.1 | 55.3 | 53.7 |
| | 24 | 55.3 | 55.3 | 52.6 |
| | 26 | 55.4 | 55.2 | 52.0 |

*The error in reporting the % 1R-cis,1'R-cis isomer in the eluent mixture, as measured by HPLC, is about 0.5-1.0%.

The stability of the cisatracurium salt in the eluent mixture at 25° C. is presented in FIG. 1 whereby two plots are compared, that is, the plot describing the stability of the 1R-cis,1'R-cis isomer in the eluent mixture of 80:10:10 dichloromethane:

DMSO:formic acid of the present invention (Column A in Table 6) vs. the plot of the dichloromethane:MeOH:benzenesulfonic acid eluent system, described in U.S. Pat. No. 5,556,978, example 2 (Column C in Table 6).

On the basis of the results given in Table 6 and FIG. 1, the amount of cisatracurium remains unchanged (taking into account the inherent error in the HPLC method) after 26 hours in the dichloromethane:DMSO:formic acid mixture. On the other hand, in the dichloromethane:MeOH:benzenesulfonic acid mixture (U.S. Pat. No. 5,556,978, example 2), the amount of cisatracurium is found to decrease by more than 3% after 26 hours.

EXAMPLE 6

This example demonstrates the chromatographic separation of (1R,1'R)-atracurium besylate isomers on semi-preparative scale.

Semi-preparative HPLC separation of a (1R,1'R)-atrcurium besylate isomer mixture was performed, as follows:
Method description:
Column: Alltech, Altima Silica, 250 mm×22 mm×5μ.
Eluent: dichloromethane:DMSO:formic acid in a ratio of 75:15:10 respectively.
Detection: 280 nm
Flow rate: 7 ml/min
Sample used: R,R'-atracurium besylate isomer mixture (consisting of about 58% 1R-cis,1'R-cis, 36% 1R-cis,1'R-trans and 6% 1R-trans,1'R-trans isomers).

490 mg of the sample of (1R,1'R)-atracurium besylate isomeric mixture was dissolved in 3 ml dichloromethane and injected into the preparative HPLC system. The fractions containing the 1R-cis,1'R-cis isomer were analyzed by HPLC against the (1R,1'R)-atracurium besylate isomer mixture reference solution. The results are summarized in Tables 7 and 8.

TABLE 7

| Fraction | Fraction volume, ml | Area of the cis-trans isomer | Total content of cis-cis isomer cation (mg) | Content of the cis-trans isomer (%)* | Total fraction purity (%)** | Isomeric fraction purity (%)*** |
| --- | --- | --- | --- | --- | --- | --- |
| 2 | 6.7 | 17.7 | 37.5 | 0.1 | 67.5 | 99.9 |
| 3 | 6.7 | 0 | 53.0 | 0 | 98.5 | 100.0 |
| 4 | 6.8 | 0 | 33.8 | 0 | 99.4 | 100.0 |
| 5 | 5.5 | 162.7 | 16.5 | 1.5 | 96.6 | 98.4 |

Note:
The trans-trans isomer is not present in the collected fractions
*Cis-trans isomer content (%) = [area of the 1R-cis,1'R-trans isomer/sum of all areas] × 100
**Total fraction purity (%) = [area of the 1R-cis,1'R-cis isomer/sum of all areas] × 100
***Isomeric purity (%) = [area of the 1R-cis,1'R-cis isomer/(area of the 1R-cis,1'R-cis isomer + area of the 1R-cis,1'R trans isomer + area of the 1R-trans,1'R-trans isomer)] × 100

TABLE 8

| No. | Isomeric purity (%) | Total purity (%) | Amount of the cisatracurium as cation (mg)-estimated by HPLC | Yield of the cisatracurium cation (%) |
| --- | --- | --- | --- | --- |
| Total loading of cis-cis isomer (as cation)-203 mg | | | | |
| 1 | 100 | >98.5 | 86.8 | 42.8 |
| 2 | >99.9 | >67.5 | 37.5 | 18.5 |
| 3 | >98 | >96.5 | 16.5 | 8.1 |
| Total | | | 140.8 | 69.4 |

Yield of >99.9% isomeric purity product = 61%. Yield of >96.5% total purity product = 51%

EXAMPLE 7A

This example demonstrates a method of performing work-up procedure for isolating the 1R-cis,1'R-cis isomer of atracurium.

The fractions from each of the three runs in Example 1 were combined and washed three times with acidified brine (pH 2 with HCl). The dichloromethane solution was dried with magnesium sulfate and evaporated to dryness to afford 680.8 mg of residual oil. The oil was dissolved in 15 ml water and the pH was adjusted to about 3 with an aqueous benzenesulfonic acid (BSA) solution. The aqueous solution was lyophilised to afford 496.3 mg of a solid which was analyzed using (HPLC). The obtained 1R-cis,1'R-cis isomer had an isomeric purity of 99.8%.

EXAMPLE 7B

This example demonstrates a method of performing work-up procedure for isolating the 1R-cis,1'R-cis isomer of atracurium.

The collected fractions mixture in an expected amount of 205 mg of the 1R-cis,1'R-cis isomer and total volume of 97 ml was washed four times with 10% brine that was acidified to pH 2 with an aqueous BSA solution and then applied to a pretreated ion exchange SAX cartridge. (The pretreatment consisted of passing 600 ml of 0.1 M of an aqueous BSA solution through the cartridge in order to substitute chloride anions with benzenesulfonate anions. Subsequently, the cartridge was conditioned by passing 300 ml of methanol followed by 300 ml dichloromethane through the cartridge). The product was retained by the cartridge and eluted from the cartridge with methanol. The methanol solution was dried over magnesium sulfate and evaporated. The residual oil was dissolved in water and the pH was adjusted to about 3 with a BSA solution. The aqueous solution was lyophilized to afford 162 mg (79% yield) of a solid containing only the 1R-cis,1'R-cis isomer.

EXAMPLE 7C

This example demonstrates a method of performing a work-up procedure for isolating the 1R-cis,1'R-cis isomer of atracurium.

(1R,1'R)-atracurium besylate isomer mixture was separated on preparative HPLC equipped with silica column using an eluate mixture of 80:10:10 dichloromethane:DMSO:formic acid. Fractions of the column eluate containing the 1R-cis,1R'-cis isomer were collected and combined to form the main fraction, as detailed in Table 9.

TABLE 9

| Total volume, ml | Total volume of the cisatracurium base, ml | % of the cis-cis isomer | % of the cis-trans isomer | % of the trans-trans isomer | Expected mount of the besylate, mg |
|---|---|---|---|---|---|
| 95 | 96.7 | 99.6 | 0.0 | 0.0 | 129.6 |

Equivalent amount of BSA was added into the main fraction and a four-step washing with aqueous acidic solution (pH=2, BSA) was carried out. The DMSO content in the obtained dichloromethane solution was 0.05% in comparison to the initial DMSO content in the eluate. The dichloromethane solution was dried over MgSO$_4$ and evaporated to dryness to afford 150.6 mg of oil, which was dissolved in water and the pH of the solution was adjusted to 3 with BSA. The aqueous solution was lyophilized to afford 109.4 mg (84% yield) of a solid. The HPLC purity of the 1R-cis,1R'-cis isomer was 97.1%, containing 0.2% of laudanosine. No 1R-cis,1R'-trans and 1R-tran,1R'-trans isomers were detected in the sample.

EXAMPLE 7D

Experiment 1 in Tables 10 and 11

This example demonstrates a method of performing a work-up procedure for isolating the 1R-cis,1'R-cis isomer of atracurium.

The cisatracurium fraction obtained from the (1R,1'R) atracurium besylate isomer mixture consisting of 55.5% 1R-cis,1'R-cis; 35% 1R-cis,1'R-trans and 5.6% 1R-trans,1'R-trans was washed four times with brine that was acidified to pH 2 with about 0.6 mM aqueous BSA solution (hereinafter the aqueous acidic solution). After separating the layers, the obtained dichloromethane solution was dried over MgSO$_4$ and evaporated under reduced pressure to obtain residual oil. The oil was mixed with a mixture of 3 ml acetone, and 12 ml of 2:1 mixture of 2-methyl-tetrahydrofurane (2-Me-THF): hexane was added. The mixture was stirred for 10 minutes and then it was cooled for 15 minutes to a temperature of about 10° C. The solvent was decanted and thick oil was obtained. The oil was dissolved in 2 ml of acetone, and 15 ml of a 1:2 mixture of 2-Me-THF:methyl tert-butyl ether (MTBE) was added and the mixture was cooled overnight at 4° C. The thus obtained precipitate was filtrated, washed with 15 ml of 2-Me-THF and dried under reduced pressure to afford a solid in 70% yield. The product was analyzed by HPLC to determine its purity and the results are detailed in Tables 10 and 11. The products of 3 additional experiments (marked as experiments 2-4) were analyzed by GC to determine the content of DMSO and the results are summarized in Table 11. The product of experiment 4 was further analyzed to determine its un-tapped bulk density, and the result was 0.37 g/ml.

TABLE 10

| No. | Description | Experiment No. 1 | 2 | 3 | 4 |
|---|---|---|---|---|---|
| 1 | Volume of acetone (1$^{st}$ addition), ml | 3 ml (without aqueous acidic solution) | 5 ml (without aqueous acidic solution) | 2.5 ml + 0.2 ml of aqueous acidic solution | 2 ml + 0.3 ml of aqueous acidic solution |
| 2 | Content of the first precipitating mixture | 2-MeTHF:hexane 2:1, 12 ml | 2-MeTHF:MTBE 1:1, 40 ml | 100 ml of 2-Me-THF | 40 ml of 2-Me-THF |
| 3 | Stirring time, minutes | 10 | 10 | 10 | 10 |
| 4 | First cooling time, minutes | 15 minutes at 10° C. | 15 minutes at 10° C. | 20 minutes at 10° C. | 20 minutes at 10° C. |
| 5 | Volume of acetone (2$^{nd}$ addition), ml | 2 | 4 ml + 1 drop of formic acid | 1 ml + 0.2 ml of aqueous acidic solution | 1 ml + 1 drop of formic acid |
| 6 | Content of the second precipitating mixture | 15 ml of 2-Me-THF:MTBE 1:2 | 2-MeTHF:hexane 5:1, 12 ml | 50 ml of 2-Me-THF | 2-MeTHF:diethyl ether 1:1, 80 ml |
| 7 | Second cooling time, minutes | Overnight at 4° C. | 30 at 10° C. | Immediate precipitation | Immediate precipitation |
| 8 | Volume of 2-Me-THF used for washing, ml | 15 | 15 | 10 | 20 ml of diethyl ether were used |
| 9 | Isomeric fraction purity, %* | 99.4 | 100 | 100 | 100 |
| 10 | Content of the cis-trans isomer, % | 0.6 | 0 | 0 | 0.2 |

The trans-trans isomer is not present in the collected fraction
*Isomeric fraction purity (%) = [area of 1R cis,1'R-cis isomer/(area of 1R-cis,1'R-cis isomer + area of 1R-cis,1'R-trans isomer + area of 1R-trans,1'R-trans isomer)] × 100

TABLE 11

| | | HPLC analysis | | | GC analysis | Yield of |
|---|---|---|---|---|---|---|
| Experiment | Product | Total fraction Purity %* | Laudanosine % | Formic acid % | DMSO (ppm) | the work up % |
| 1 | Initial | 91.2 | 3.5 | — | — | 70 |
| | Final | 93.2 | 1.2 | 0.5 | 324 | |

TABLE 11-continued

| Experiment | Product | HPLC analysis | | | GC analysis | Yield of the work up % |
| | | Total fraction Purity %* | Laudanosine % | Formic acid % | DMSO (ppm) | |
|---|---|---|---|---|---|---|
| 2 | Initial | 99.2 | <0.1 | — | — | 69 |
|   | Final | 98.9 | 0.5 | 1.3 | 650 | |
| 3 | Initial | 87.1 | 0.4 | — | — | 74 |
|   | Final | 90.0 | 0 | 0.2 | 41 | |
| 4 | Initial | 92.6 | 0.6 | — | — | 77 |
|   | Final | 93.3 | 0.4 | 0.7 | 459 | |

*Total fraction purity (%) = [area of 1R cis,1'R-cis isomer/sum of all areas] × 100

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of obtaining the 1R-cis,1'R-cis isomer from a (1R,1'R)-atracurium isomer mixture, the method comprising separating the mixture by normal phase, preparative HPLC using a non-aqueous eluent comprising an organic solvent, a polar aprotic co-solvent and a weak acid having a pKa value of 2.5 or higher.

2. The method of claim 1, comprising:
    (a) dissolving the (1R,1'R)-atracurium salt isomer mixture in at least one organic solvent;
    (b) applying the isomer mixture solution to a preparative HPLC column containing a normal stationary phase;
    (c) eluting the column with the eluent;
    (d) collecting one or more fractions containing the 1R-cis, 1'R-cis isomer;
    (e) optionally performing an ion exchange step; and
    (f) isolating the 1R-cis,1'R-cis isomer.

3. The method of claim 2, wherein the organic solvent of step (a) comprises dichloromethane, chloroform, 1,4-dioxane or a mixture thereof.

4. The method of claim 3, wherein the organic solvent of step (a) comprises dichloromethane.

5. The method of claim 2, wherein the concentration of the (1R,1'R)-atracurium salt isomer mixture in the organic solvent in step (a) is from 0.1 M to 0.5 M.

6. The method of claim 2, wherein the organic solvent of the mobile phase of step (c) comprises dichloromethane, chloroform, 1,4-dioxane, or a mixture thereof.

7. The method of claim 6, wherein the organic solvent of the mobile phase of step (c) comprises dichloromethane.

8. The method of claim 2, wherein the polar aprotic co-solvent of the mobile phase of step (c) comprises dimethyl sulfoxide (DMSO), N,N-dimethylformamide (DMF), N,N-dimethylacetamide (DMA), N-methyl-2-pyrrolidone (NMP) or a mixture thereof.

9. The method of claim 8, wherein the polar aprotic co-solvent of the mobile phase of step (c) comprises DMSO.

10. The method of claim 2, wherein the weak acid of step (c) comprises formic acid, acetic acid, propionic acid or a mixture thereof.

11. The method of claim 10, wherein the weak acid comprises formic acid.

12. The method of claim 2, wherein the solvent mixture for eluting the column in step (c) comprises dichloromethane, DMSO and formic acid in a ratio ranging from 70-85% vol. (dichloromethane):8-20% vol. (DMSO):5-15% vol. (formic acid).

13. The method of claim 2, wherein the ion exchange of step (e) comprises contacting an eluted material with an ion exchange resin.

14. The method of claim 2, wherein isolation step (f) comprises the steps of:
    (a) combining eluted fractions containing at least 90% of the 1R-cis,1'R-cis isomer;
    (b) washing the combined eluted fractions with acidic brine and separating the phases;
    (c) drying the organic phase and evaporating the solvent to obtain a residual oil;
    (d) dissolving the oil in a solvent; and
    (e) isolating the product by lyophilizing the solution or by precipitation.

15. The method of claim 14, wherein the solution used for washing is a 10% brine solution acidified with benzenesulfonic acid (BSA).

16. The method of claim 14, wherein the product is precipitated at least once by adding at least one solvent selected from tetrahydrofuran (THF), 2-methyl-tetrahydrofuran (2-Me-THF), diethyl ether, diisopropyl ether, methyl tert-butyl ether (MTBE), acetone, hexane, heptane, cyclohexane, and mixtures thereof.

17. The method of claim 16, wherein the solvent or solvent mixture contains formic acid or brine acidified with BSA.

18. The method of claim 2, further comprising subjecting the isolated product to ion exchange via a strong anion exchange column or cartridge (SAX).

19. The method of claim 2, wherein the eluent system comprises dichloromethane, DMSO and formic acid, and the content of the 1R-cis,1'R-cis isomer in the eluent system remains unchanged after 26 hours at room temperature.

20. The method of claim 2, wherein the isolated 1R-cis,1'R-cis isomer has an isomeric purity greater than 99.5%.

21. The method of claim 20, wherein the (1R,1'R)-atracurium salt isomer mixture is a (1R,1'R)-atracurium besylate isomer mixture, and the isolated 1R-cis,1'R-cis isomer is cisatracurium besylate.

* * * * *